(12) United States Patent
Weinberg et al.

(10) Patent No.: US 9,995,810 B2
(45) Date of Patent: Jun. 12, 2018

(54) APPARATUS AND METHOD FOR DECREASING BIO-EFFECTS OF MAGNETIC GRADIENT FIELD GRADIENTS

(71) Applicants: WEINBERG MEDICAL PHYSICS LLC, Bethesda, MD (US); Irving N. Weinberg, Bethesda, MD (US); Pavel Stepanov, North Potomac, MD (US)

(72) Inventors: Irving N. Weinberg, Bethesda, MD (US); Pavel Stepanov, North Potomac, MD (US)

(73) Assignee: Weinberg Medical Physics Inc, North Bethesda, MD (US)

( * ) Notice: Subject to any disclaimer, the term of this patent is extended or adjusted under 35 U.S.C. 154(b) by 1373 days.

(21) Appl. No.: 13/917,712

(22) Filed: Jun. 14, 2013

(65) Prior Publication Data

US 2013/0271136 A1    Oct. 17, 2013

Related U.S. Application Data

(63) Continuation-in-part of application No. 12/905,256, filed on Oct. 15, 2010, now Pat. No. 8,466,680, which is a continuation-in-part of application No. 12/488,105, filed on Jun. 19, 2009, now Pat. No. 8,154,286.

(60) Provisional application No. 61/074,397, filed on Jun. 20, 2008.

(51) Int. Cl.
| | |
|---|---|
| *G01V 3/00* | (2006.01) |
| *G01R 33/54* | (2006.01) |
| *G01R 33/28* | (2006.01) |
| *G01R 33/385* | (2006.01) |

(52) U.S. Cl.
CPC ........... *G01R 33/54* (2013.01); *G01R 33/28* (2013.01); *G01R 33/385* (2013.01); *G01R 33/3852* (2013.01); *G01R 33/288* (2013.01)

(58) Field of Classification Search
CPC .................................................. G01R 33/288
USPC ........................................ 324/309, 307, 314
See application file for complete search history.

(56) References Cited

U.S. PATENT DOCUMENTS

| | | | |
|---|---|---|---|
| 5,235,279 | A | 8/1993 | Kaufman et al. |
| 5,311,135 | A | 5/1994 | Vavrek et al. |
| (Continued) | | | |

OTHER PUBLICATIONS

Hodgkin et al.; A quantitative description of membrane current and its application to conduction and excitation in nerve; J. Physiol.; 1952; pp. 500-544; vol. 117.

(Continued)

*Primary Examiner* — Louis Arana
(74) *Attorney, Agent, or Firm* — Barnes & Thornburg LLP (57) ABSTRACT

A magnetic field generator includes a power source and a segmented or un-segmented coil connected to the power source to generate a time-varying magnetic field. Energy is applied to the coil so that the coil generates a time-varying magnetic field gradient with a magnitude of at least 1 milliTesla per meter and a rise-time of less than 1000 microseconds. The coil may be comprised of overlapping, non-overlapping or partially overlapping coil segments that may individually energized to further improve the operating characteristics of the coil to further decrease bio-effects in magnetic resonance imaging through the use of reduced pulse lengths and multi-phasic magnetic gradient pulses.

15 Claims, 9 Drawing Sheets

(56) References Cited

U.S. PATENT DOCUMENTS

| | | | |
|---|---|---|---|
| 6,198,282 B1 * | 3/2001 | Dumoulin | G01R 33/3852 324/307 |
| 6,418,336 B1 | 7/2002 | Kimmlingen et al. | |
| 6,630,829 B1 | 10/2003 | Liu | |
| 2010/0308829 A1 * | 12/2010 | Vu | G01R 33/288 324/314 |

OTHER PUBLICATIONS

MacCabee; Influence of pulse sequence, polarity and amplitude on magnetic stimulation of human and porcine peripheral nerve; J. Physiol.; 1998; pp. 571-585; vol. 513.

Schaefer et al.; Review of Patient Safety in Time-Varying Gradient Fields; J. Magnetic Resonance Imaging; 2000; pp. 20-29; vol. 19.

* cited by examiner

APPARATUS AND METHOD FOR DECREASING BIO-EFFECTS OF MAGNETIC GRADIENT FIELD GRADIENTS

CROSS-REFERENCE TO RELATED APPLICATION(S)

This application is a continuation-in-part of U.S. patent application Ser. No. 12/905,256, filed Oct. 15, 2010, which a continuation-in-part of U.S. patent application Ser. No. 12/488,105, filed Jun. 19, 2009, now U.S. Pat. No. 8,154,286, which relies for priority on U.S. Provisional Application No. 61/074,397 filed Jun. 20, 2008, the contents of which are incorporated herein by reference.

FIELD OF THE INVENTION

The present invention concerns an apparatus and a method for decreasing the bio-effects of magnetic field gradients on tissue(s). More specifically, the present invention concerns an apparatus and a method to decrease bio-effects on neurological tissue from magnetic field gradients, such as those experienced during Magnetic Resonance Imaging ("MRI").

DESCRIPTION OF RELATED ART

As should be appreciated by those skilled in the art, MRI is a technology whereby a magnetic field gradient is applied to tissue to generate a response from the atoms and molecules in the tissue. After detection of the response, and an image of the tissue is generated based on that response.

The magnetic field gradient affects the tissue at an atomic and/or molecular level, which is a desirable outcome of the magnetic stimulation.

Unfortunately, magnetic field gradients also elicit undesirable responses from tissue. In particular, neurological tissue generates, receives, and transmits electrical signals, and, as the laws of physics dictate, changing magnetic fields can cause electrical field generation and consequent neurological stimulation. Accordingly, the effect of magnetic field gradients on neurological tissue is especially pronounced by comparison with other tissue types.

A model for gradient-induced bio-effects was described by D R McNeal and J P Reilly in the mid to late 1970's (DR McNeal, "Analysis of a model for excitation of myelinated nerve," in IEEE Trans. Biomed. Eng., 23:329-337, 1976; and J P Reilly, "Electric and Magnetic field coupling from high voltage AC power transmission lines—Classification of short-term effects on people," in IEEE Trans. on Power Apparatus and Systems, 97(6): 2243-2252, 1978) based on classic membrane-excitability relations (A L Hodgkin and A F Huxley, "A quantitative description of membrane current and its application to conduction and excitation in nerve," in J. Physiol., 117:500-544, 1952).

Subsequent elaborations of the model were disclosed by Reilly in "Sensory effects of transient electrical stimulation: Evaluation with a neuroelectric model," IEEE Trans. Biomed. Eng., 32(19) 1001:1011, 1985.

The model elaborated by Reilly invokes the telegraph equation first applied in the late 1800's to design trans-Atlantic cables.

As in underwater cables, neurons are organized in sections that are separated by nodes of Ranvier. These nodes enforce resistance/capacitance ("RC") equations that govern neuronal behavior, with time constants related to neuronal diameter and inter-nodal distances.

Having provided a brief overview of the electrical characteristics, attention is now turned to magnetic field gradients.

At least with respect to MRI, magnetic field gradients have several components of particular interest. The first is the magnitude (referring to the maximum magnitude of the gradient field), which is typically measured in milliTeslas (mT). Another important quantity is the gradient strength, which is typically measured in milliTeslas per meter (mT/m). Further descriptors include the duration, rise-time and fall-time of the gradient, which are typically measured in milliseconds (ms) or in microseconds (μs). Another key descriptor is the slew rate (referring to the magnitude of the change of the gradient field in time), which is typically measured in Teslas per meter per second (T/m/s).

As the laws of physics dictate, changes in magnetic fields result in the generation of electrical fields. Changes in magnetic field gradients in tissue, therefore, also result in the formation of electric fields.

When studying neurological tissues, the changes in magnetic field gradients depolarize nerves, once a threshold is reached. This threshold becomes higher as the pulse duration becomes shorter. The relationship between these variables follows a traditional, hyperbolic curve.

It is noted that experimental studies in humans (D. J. Schaefer, J. D. Bourland, and J. A. Nyenhuis, "Review of Patient Safety in Time-Varying Gradient Fields," in J. Magnetic Resonance Imaging, 19:20-29, 2000) have validated the basic model for pulse durations as short as fifty microseconds.

In response to various MRI studies, regulatory agencies have codified the strength-duration model into law, at least in Europe and the United States. (See Requirements for the Safety of MR Equipment for Medical Diagnosis, IEC 60601-2-33 (with respect to Europe); see also Guidelines for Premarket Notifications for MR Diagnostic Devices, 21 C.F.R. § 807.87 (with respect to the US).)

As a result of these studies and as a result of the regulations that are based on these studies, MRI manufacturers have attempted to design triangular pulse sequences to conform to the limits prescribed by the Reilly model, among others.

One such attempt is described in U.S. Pat. No. 6,198,282, which is directed to an optimized gradient system for providing minimum-duration gradient pulses, the contents of which are incorporated herein by reference.

The prior art also includes evidence of interest in the strength-duration curve from another direction, as manufacturers of neuron-stimulators try to shape the pulse in order to increase stimulation. (See P. J. Maccabee, "Influence of pulse sequence, polarity and amplitude on magnetic stimulation of human and porcine peripheral nerve," J. Physiol., 513:571-585, 1998).

As a result of numerous studies and advancements, those in the industry traditionally have applied magnetic field gradients above a threshold for neuronal stimulation. To minimize neuronal stimulation, the duration of the magnetic field gradient has been extended. A longer duration helps to minimize the impact of the magnetic field gradient on the neurological tissue. One immediately apparent downside to this approach is that the MRI diagnostic requires a substantial amount of time.

There appears to be wide acceptance in the MRI community in the belief that the attainment of high gradient slew rates (i.e., the change in magnetic gradients over a short period of time) would be a welcome development for the industry.

As should be immediately apparent, one impetus for increasing slew rates is to reduce scan time. It is postulated that, if a given MRI sequence requires a certain number of pulses, then the application of shorter pulses would permit the MRI sequence to be completed in a shorter time period (i.e., faster) than conventional techniques.

Among other benefits, saving time improves safety for unstable patients. Saving time also may reduce the cost of the MRI sequence.

A second incentive for increasing slew rate is to increase gradient field strength, which improves spatial resolution. For a given prescribed pulse sequence, the faster one can ramp up the magnetic field per pulse, the higher the gradient strength will be for the same overall scan time. Since the gradient strength is proportional to the spatial resolution of the MRI image obtained, a higher slew rate will result in a better spatial resolution. Increased spatial resolution may improve medical diagnosis in some cases.

As discussed above, for manufacturers of MRI devices, limits have been set for slew rates based on studies concerning the presence of bio-effects due to neuronal stimulation. These limits have placed a limit on currently-available scanning technologies.

As also should be appreciated by those skilled in the art, the generation of a magnetic field gradient with a very small duration presents technological challenges as well. Accordingly, there also has been a technological barrier to decreasing the duration of the magnetic field gradient.

With respect to technological limitations, in some MRI devices, switches are used to trigger the generation of a magnetic field gradient. The types of switches traditionally used include Insulated-Gate Bipolar Transistor ("IGBT") and Metal Oxide Semiconductor Field Effect Transistor ("MOSFET")-based devices. However, these traditional switches are not capable of creating magnetic filed gradients with a sufficiently short duration to avoid neuronal stimulation.

Recent developments in switches offer a solution to the technological problem experienced with prior art MRI devices.

Specifically, several generations of plasma physics experimentalists have led the development of reliable solid-state switches and pulse-forming lines that are just now being introduced into the community. (See H. Sanders and S. Glidden, "High Power Solid State Switch Module," in International Power Modulator Symposium Conference Record, pp. 563-566, 2004).

Those switches are capable of triggering pulses of ten-thousand amps in one microsecond, orders of magnitude higher than the IGBT and MOSFET-based systems currently employed in commercial gradient field generators for MRI systems (See D. A. Seeber, J. H. Hoftiezer, and C. H. Pennington, "Pulsed current gradient power supply for microcoil magnetic resonance imaging," in Magnetic Resonance Engineering, 15(3): 189-200, 2002).

It is axiomatic in the field of pulsed power technology that it is often easier to close a switch than to open a switch. To take advantage of this physical parameter, solid-state switches may be combined with pulse-forming lines ("PFLs").

PFLs, which are also known as Blumlein lines (named for the World-War II-era inventor David Blumlein), are dielectric-filled transmission lines that begin draining their charge when triggered by a solid-state switch. The transmission lines stop delivering current once the dielectric has been drained of charge. Blumlein lines can switch in nanoseconds, and maintain currents for milliseconds. (K Gasthaus, "A millisecond Blumlein line for the power supply of a high power laser," in J. Phys. E: Instrum., 20:192-195, 1987). In order to deliver pulses of varying widths, sets of PFLs may be triggered independently of one another into a common load.

In view of the foregoing, there exists a desire to apply higher magnetic field gradients to tissue in an MRI environment while avoiding adverse bio-effects on that tissue.

SUMMARY OF THE INVENTION

Therefore, disclosed embodiments provide an apparatus and a method for decreasing the duration of scan times for MRI. Disclosed embodiments also involve the application of magnetic field gradients with a magnitude greater than that traditionally employed. In one embodiment, the gradient slew rate may be up to hundreds of times greater than previously applied. In other embodiments, the magnitude may be greater.

Disclosed embodiments may decrease bio-effects from magnetic field gradients by applying a magnetic field gradient to tissue within a time frame below the response threshold for that tissue.

BRIEF DESCRIPTION OF THE DRAWINGS

The invention will now be described in connection with the drawings appended hereto, in which.

DESCRIPTION OF THE INVENTION

Inventive concepts will now be described in connection with one or more embodiments. It is intended for the embodiments to be representative of the invention and not limiting of the scope of the invention. The invention is intended to encompass equivalents and variations, as should be appreciated by those skilled in the art.

Disclosed embodiments take advantage of a physiological loophole: according to accepted physiological models for ionic channel transport, bi-phasic pulses on the order of a microsecond are too fast for the nerve to change its polarization state, and are, therefore, effectively ignored. Disclosed embodiments capitalize on this physiological loophole. According to the model elaborated by Reilly, this loophole implies that gradient field thresholds may be increased by factors of five or more above the usual hyperbolic model without triggering any bio-effects.

Disclosed embodiments also takes advantage of magnetic pulse delivery systems that are more powerful than traditional systems used to deliver MRI pulses.

At least one disclosed embodiment may utilize solid-state switches and/or PFL technologies that conform to the requirements of MRI gradient amplifiers. These requirements include increased repetition rates, impedance and trigger matching to MRI pulse programming consoles, and electrical/acoustic noise shielding considerations. Downstream modifications include the buttressing of gradient coils to handle the higher electromagnetic (i.e., J×B) forces that will occur at higher current loads, especially in high resolution MRI systems with high static magnetic fields.

According to classic coil-design codes, eddy current shielding is likely to be less of a problem than at current regimes, and reductions in inductance are predicted. The influence of eddy currents may further be minimized by acquiring signals at long TE, when eddy currents have died down, as contemplated by still another embodiment of the present invention.

At least one disclosed embodiment may make the bore of the cryostat significantly larger than the gradient coil, further reducing the influence of eddy currents. With respect to mechanical stabilization requirements, although the magnetic forces and torques (i.e., J×B) will be high, the durations will be so short that the delivered impulse can be handled with minimal mechanical stabilization over existing systems.

As a prelude to the discussion of the various embodiments of the present invention, a general discussion of MRI devices is now provided. This overview is not intended to be limiting of the invention. It is provided merely to assist with an understanding of the components of the various embodiment of the present invention, as detailed below.

As a general rule, an MRI device includes a magnetic field generator, typically a magnetic coil and a radio frequency ("RF") generator or transmitter. The magnetic coil generates a magnetic field and the RF generator emits radio waves.

As should be appreciated by those skilled in the art, tissue is primarily composed of water molecules, each of which contains hydrogen atoms. When a person's tissue is exposed to a strong magnetic field, the hydrogen atoms align with the direction of the magnetic field. Subsequently, the RF generator emits radio waves to the hydrogen atoms while in the aligned state. Some of the energy from the radio waves is absorbed by the hydrogen atoms in the water molecules, thereby altering the magnetic alignment of the hydrogen atoms. The altered magnetic state is detected by the detector, which generates signals that are processed to form as an image.

Figure 1:
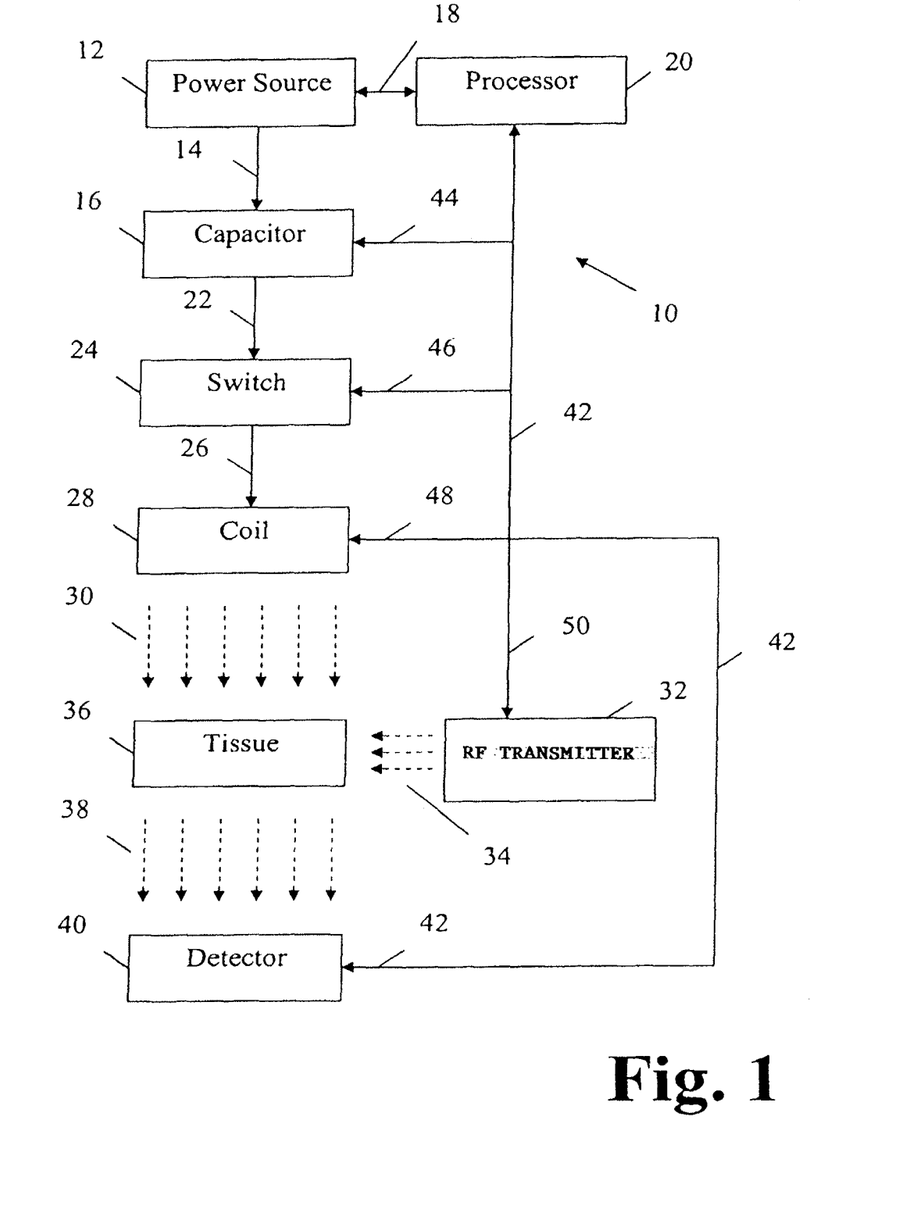
FIG. 1 is a schematic illustration of a first embodiment of an apparatus contemplated by disclosed embodiments.

With this overview in mind, reference is now made to FIG. 1. FIG. 1 provides a schematic diagram of a first contemplated embodiment of a MRI device 10 designed according to this disclosure The MRI device 10 includes a power source 19. The power source 19 may be any type of generator suitable for generating power to be provided to the one or more of the components connected thereto. The generator may provide an alternating current (AC) or a direct current (DC), as should be appreciated by those skilled in the art. The precise output of the power source 19 is not critical to the operation of the present invention. Moreover, the power output, once generated, may be converted different types (e.g., AC or DC) as required by individual components of the system.

In FIG. 1, the power source 19 is illustrated as providing power to each of the various components of the MRI device 10 of the present invention. It is noted, however, that the depicted arrangement is meant to be illustrative only. As should be appreciated by those skilled in the art, the individual components of the MRI device 10 may receive power from a centralized source, such as the power source 19. Alternatively, the various components may receive power from alternative power sources. Accordingly, the depiction of a single power source 19 is not intended to be limiting of the invention.

In addition, as detailed below, the MRI device 10 of the present invention is illustrated and discussed with reference to single communication lines (or links) extending between the various components. The illustration of single communication lines is meant to simplify the discussion and illustration of the various embodiments of the invention. As should be appreciated by those skilled in the art, there may be multiple communication lines between the various components of the MRI device 10 as required for their operation. Moreover, the communication lines are not intended to be limited to wired links. To the contrary, the communication lines may be wireless, as required or desired for operation of the MRI device 10.

In one contemplated embodiment of the present invention, the power source 19 may include a plurality of power sources 19, each of which generates power with different characteristics, as required by the device(s) and/or components associated therewith.

As depicted in FIG. 1, power from the power source 19 travels in two directions. Power from the power source 19 is conducted first along a communication line 14 to a capacitor 16. Power from the power source 19 is carried second along a communication line 18 to a processor 20.

The capacitor 16 may be of any size or type as would be appreciated by those skilled in the art. As is its nature, the capacitor 16 stores a charge based on the power inputted from the power source 19. That charge is eventually discharged, as discussed in greater detail below.

While FIG. 1 illustrates a single capacitor 16, a plurality of capacitors 16 may be employed without departing from the scope of the present invention. In one contemplated embodiment, the MRI device 10 relies upon a plurality of capacitors 16 for its operation. As should be appreciated by those skilled in the art, plural sets of capacitors 16 may be employed to generate successive magnetic field gradients.

In the second flow path, power from the power source 19 is provided to the processor 20. The processor 20 may be of any type suitable for executing instructions, generating data, receiving data, storing data, and the like. In one contemplated embodiment, the processor 20 may be a personal computer. In other embodiments, the processor 20 may be a mainframe computer, a portable computer, a personal data assistant ("PDA") or any other similar device. The exact design and functionality of the processor 20 is not critical to operation of the present invention. Accordingly, the processor 20 may be of any type suitable for the operation of the MRI device 10.

The capacitor 16 is connected, via a communication line 22, to a switch 24. Accordingly, when the capacitor 16 discharges the stored charge, the stored charge passes through the communication line 22 to the switch 24.

The switch 24 is connected, via a communication line 26, to a coil 28. Accordingly, when the capacitor 16 is discharged, energy from the capacitor 16 is passed to the coil 28, which generates a magnetic field 30.

The coil 28 need not be a single coil. To the contrary, it is contemplated that the coil 28 may include a plurality of coils 28, each of which is capable of generating all or part of the magnetic field 30. Moreover, as should be appreciated by those skilled in the art, where plural coils 28 are employed, the coils 28 need not be of the same type or size. To the contrary, it is contemplated that, where plural coils 28 are employed, they may be differ from one another to produce magnetic field gradients of differing magnitudes, periods, etc.

As also shown in FIG. 1, the MRI device 10 includes an RF transmitter 32. As discussed briefly above, the RF transmitter 32 generates radio waves 34. While one RF transmitter 32 is illustrated, it is contemplated that a plurality of RF transmitters 32 may be employed without departing from the scope of the present invention. Moreover, where plural RF transmitters 32 are employed, they may be of different sizes, types, etc.

As illustrated, the magnetic field 30 and the RF waves 34 are directed at a tissue sample 36. While the tissue sample 36 may be a portion of an organism, it may also be a complete organism.

After interaction of the magnetic field 30 and the RF waves 34 with the tissue 36, the tissue 36 generates a responsive signal 38 that is detected by the detector 40. As should be appreciated by those skilled in the art, the signal 38 may encompass a multitude of different signals from the tissue 36. The detector 40 detects the signals 38 and passes the signals 38 to the processor 20 via the communication line 42. The processor 20 receives and processes the signals 38 to generate an image representative of the composition of the tissue 36.

As should be appreciated by those skilled in the art, the processor 20 may not be the device that processes the signals 38 to generate the image of the tissue 36. To the contrary, the detector 40 may be combined with a suitable imaging device. In still another embodiment, the imager may be a component separate from the processor 20 and the detector 40. Still further embodiments are contemplated to fall within the scope of the present invention.

With continued reference to FIG. 1, the MRI device 10 includes communication line 42. Communication line 42 is illustrated as a central bus that connects the processor 20 to the capacitor via communication line 44, to the switch, via communication line 46, to the coil, via communication line 48, and to the RF transmitter, via communication line 50. A central bus, however, is not required to practice the invention. To the contrary, multiple connections may be established between the components of the MRI device 10 without departing from the scope of the invention, as discussed above.

It is noted that the communication lines 14, 18, 22, 26, 42, 44, 46, 48, 50 all may conduct data and/or power. The communication lines, therefore, are meant to illustrate multi-modal connections between the various components of the MRI device 10. As noted above, each of the communication lines 14, 18, 22, 26, 42, 44, 46, 48, 50 may be replaced with one or more separate connections, as required or desired. The communication lines 14, 18, 22, 26, 42, 44, 46, 48, 50 may be unidirectional or bidirectional as required or desired.

With respect to the communication lines 42, 44, 46, 38, 50, it is contemplated that the processor 20 will provide operating instructions to one or more of the components to which it is connected. The processor 20, therefore, is contemplated to incorporate control functionality over one or more of the components, as should be appreciated by those skilled in the art. It is also contemplated that controls may be fed from one component to another, as required or desired for operation of the MRI device 10.

Figure 2:
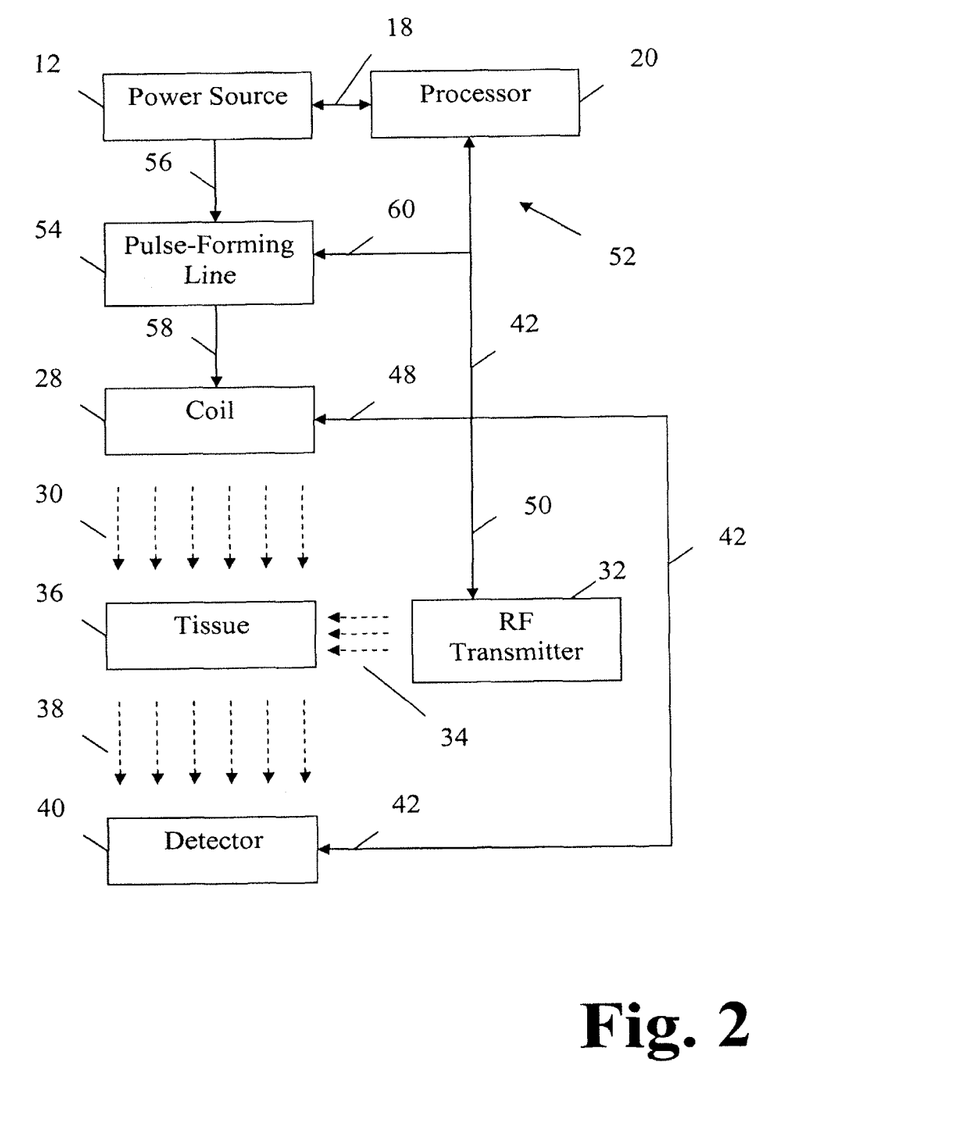
FIG. 2 is a schematic illustration of a second implementation of an apparatus contemplated by disclosed embodiments.

FIG. 2 illustrates an MRI device 52, which is a second embodiment contemplated by the present invention. Many of the components of the MRI device 52 are the same as illustrated and described in connection with MRI device 10 in FIG. 1. As a result, those components are provided with the same reference numbers as the components in FIG. 1. Moreover, the descriptions of these components is not repeated for the sake of brevity.

The MRI device in FIG. 2 differs from the MRI device 10 in FIG. 1 in at least one respect. Specifically, the capacitor 16 and the switch 24 have been replaced with a pulse-forming line 54. The pulse forming line 54 is connected to the power source 19 via communication line 56. The pulse forming line 54 is connected to the coil 28 via the communication line 58. The pulse forming line 54 connects to the processor via the communication line 60.

As discussed above, a pulse forming line 54 is also known as a Blumlein line. Pulse forming lines 54 are transmission lines that begin draining their charge in response to a triggering event, such as when triggered by a solid-state switch. Pulse forming lines 54 also are referred to as pulse forming networks. A pulse forming network ("PFN") accumulates electrical energy over a predetermined period of time and releases the electrical energy in the form of a square pulse in a relatively short period of time, depending upon the materials that make up the PFN 54. PFNs 54 also may be engineered to provide pulsed power. A PFN 54 may be charged by a high voltage power source 19 and then rapidly discharged (possibly via a high voltage switch).

The pulse forming line 54 may be a single line or may be a plurality of lines combined together. The pulse forming line 54 also may be a pulse forming network 54, as discussed above. The exact composition and construction of the PFN 54 is not critical to operation of the present invention.

Figure 3:
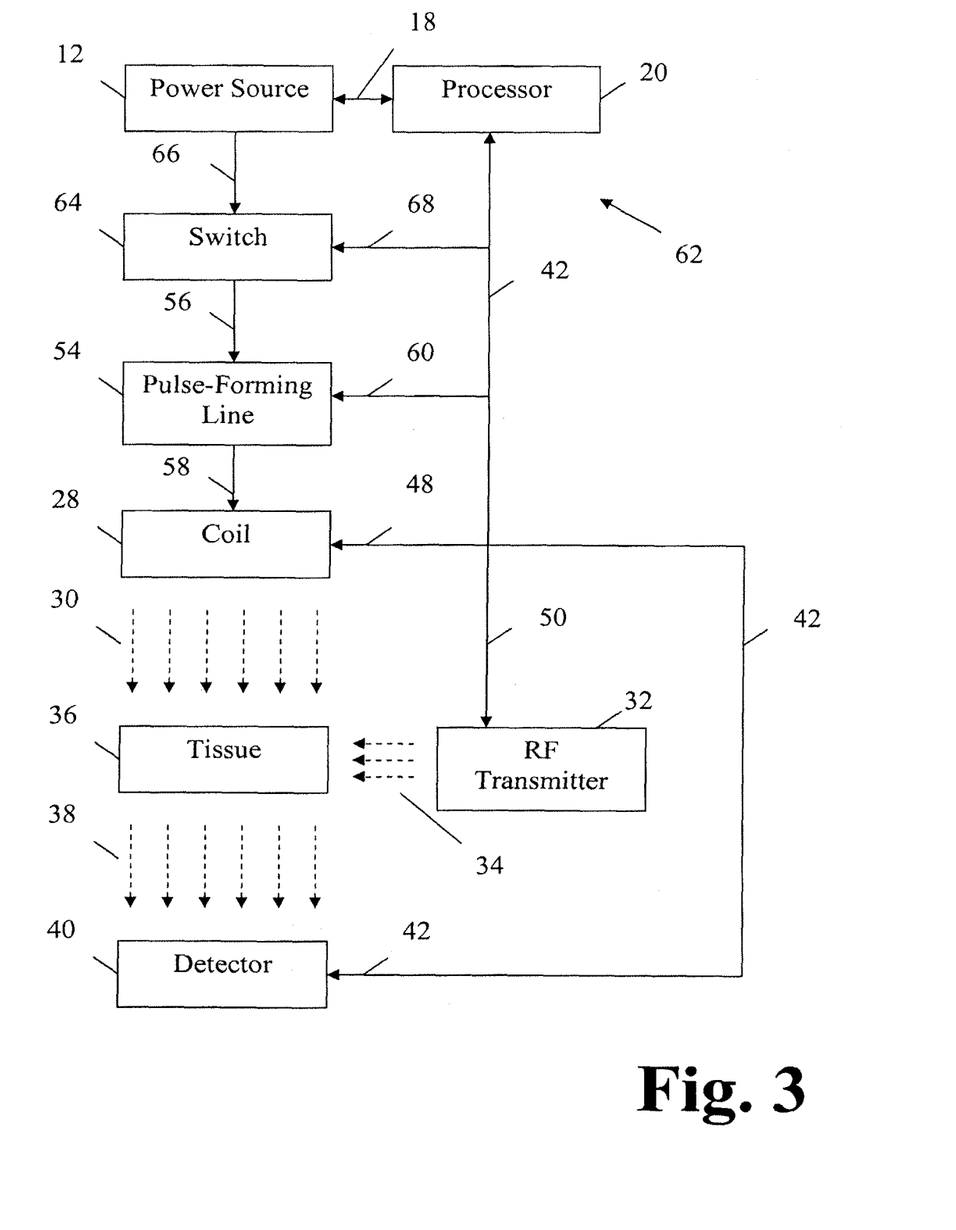
FIG. 3 is a schematic illustration of a third implementation of an apparatus contemplated by disclosed embodiments.

FIG. 3 illustrates a third embodiment of an MRI device 62. This embodiment is similar to the MRI device 52 illustrated in FIG. 2. In this third embodiment, however, a switch 64 has been added between the power source 19 and the pulse forming line 54. As illustrated, the power source is connected to the switch via a communication line 66. The switch 65, in turn, is connected to the processor 20 via the communication line 68. As noted above, the switch 65 may be employed to trigger the pulse forming line 54 to release its energy to the coil 28.

Figure 4:
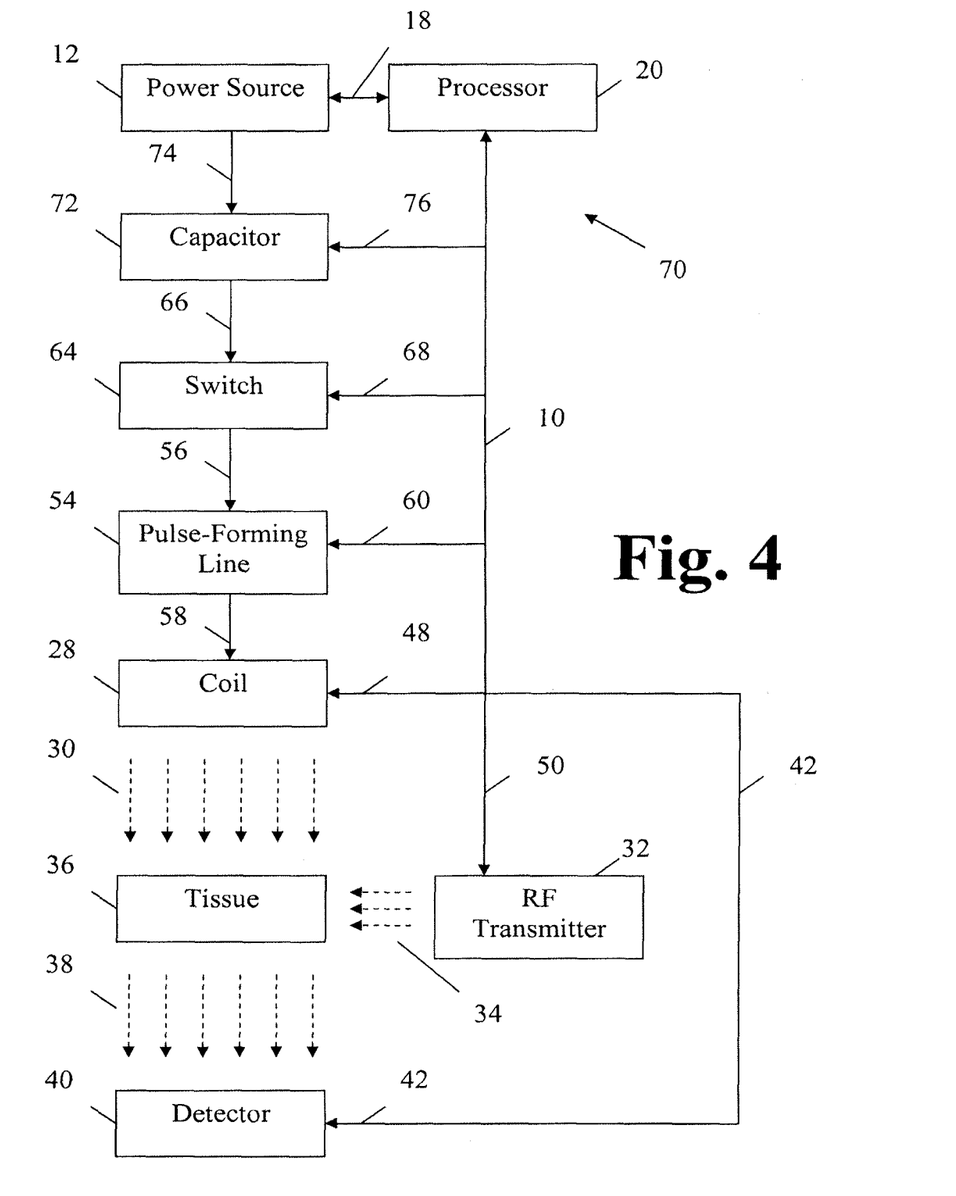
FIG. 4 is a schematic illustration of a fourth implementation of an apparatus contemplated by disclosed embodiments.

FIG. 4 illustrates a fourth embodiment of an MRI device 70. This fourth embodiment is a modification of the MRI device 62, which is illustrated in FIG. 3. Here, a capacitor 72 has been inserted between the switch 64 and the power source 19. The capacitor 72 connects to the power source via the communication line 74. The capacitor 72 connects to the processor via the communication line 76. In this embodiment, it is contemplated that the capacitor 72 will discharge power to the switch 64, which will discharge power through the pulse forming line 54 to the coil 28, as illustrated.

With respect to the embodiments illustrated in FIGS. 1, 2, 3, and 4, and for purposes of the present invention, the connection between the power source 19 and the coil 28 is considered to be a controlled communication line. As a result, the embodiments provide variations for contemplated constructions of that controlled communication line.

Figure 5:
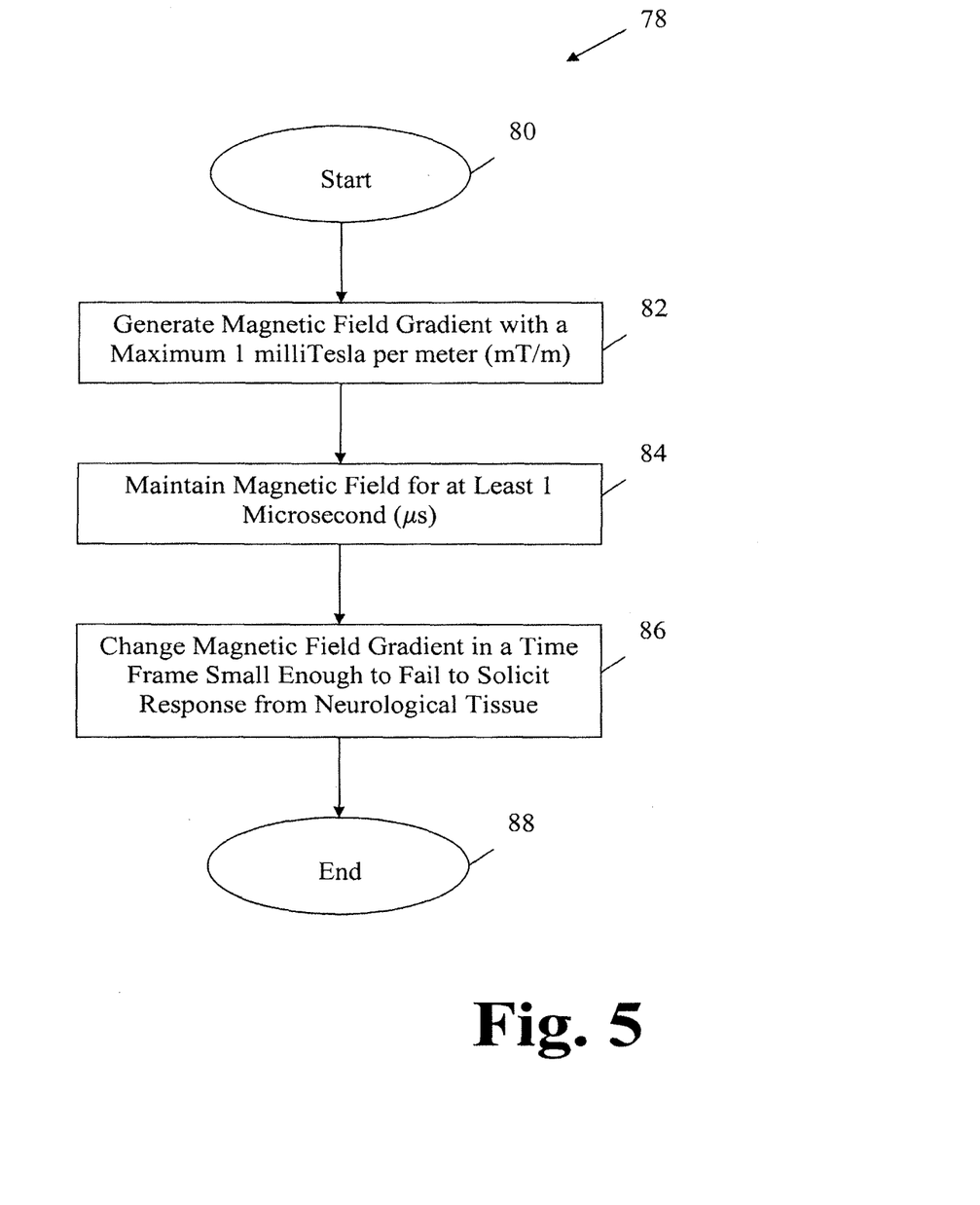
FIG. 5 is a flow chart illustrating one method contemplated by disclosed embodiments.

FIG. 5 illustrates a method 78 contemplated by the present invention. The method 78 starts at 80 and ends at 88. Following the start 80, at 82, a magnetic filed gradient with a maximum of 1 milliTesla per meter (mT/m) is generated. At 84, the magnetic field gradient is maintained for a least about 1 microsecond and up to about 10 microseconds. At 86, the magnetic field gradient is changed in a time frame small enough to fail to solicit a response from neurological tissue. The method 78 ends at 88.

It is contemplated by the present invention that the application of a magnetic field gradient of no more than 1 mT/m will avoid triggering a biological response from neurological tissue. It is also contemplated that application of the magnetic field gradient for less than about 10 microseconds also will establish suitable conditions to avoid triggering a biological response from neurological tissue.

Figure 6:
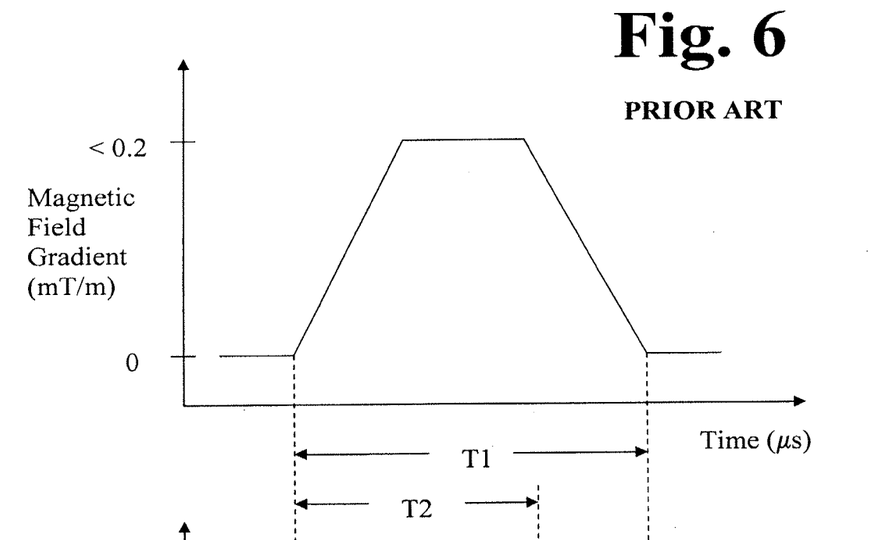
FIG. 6 is a graph depicting the magnetic field gradient and duration typical of a prior art MRI device.

FIG. 6 is a graphical illustration of a single magnetic field gradient pulse according to the prior art. As illustrated, the duration T1 of the magnetic field gradient pulse exceeds a neurological response time T2 for neurological tissue. In addition, the magnitude of the magnetic field gradient pulse is less than about 0.2 mT/m.

Figure 7:
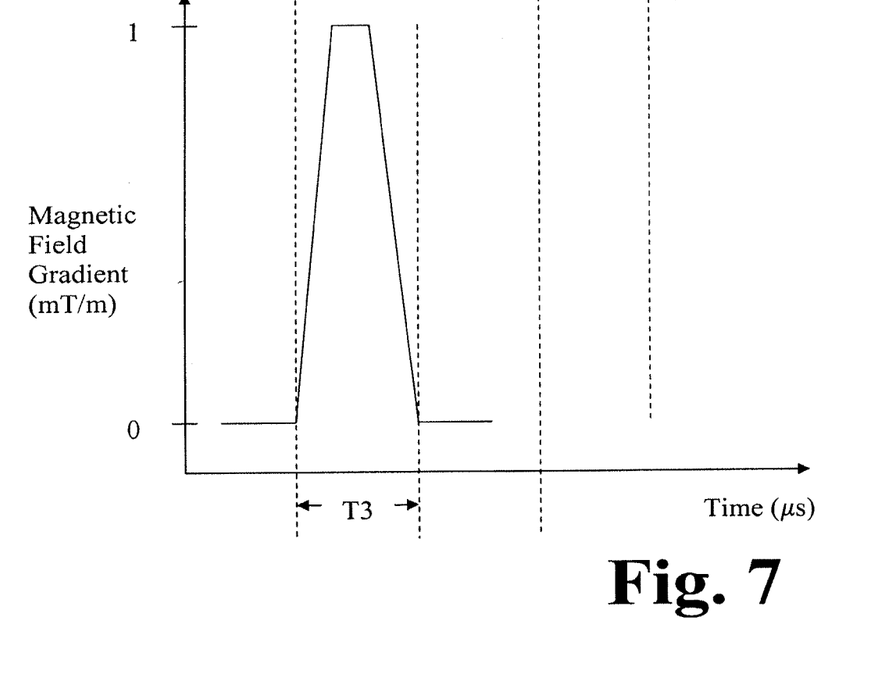
FIG. 7 is a graph depicting the magnetic field gradient and duration contemplated by disclosed embodiments.

FIG. 7 provides a graphical illustration of a magnetic field gradient pulse generated according to the present invention. The pulse duration T3 is less than the pulse duration T1 according to the practice in the prior art. Also, the pulse duration T3 is less than the neurological response time T2. In keeping with the invention, the pulse duration T3 is less than about 10 microseconds, which is considered to be appropriate for avoiding a neurological response. In one contemplated embodiment, the pulse duration T3 is about 1 microsecond.

A comparison between FIGS. 6 and 7 also illustrate one further aspect of the present invention. Specifically, the magnetic field gradient as generated by the prior art is about 5 times weaker than the magnetic field gradient generated by the MRI device 10 of the present invention.

As discussed, the magnetic pulses are created by releasing electrical charge stored in capacitors and/or transmission lines into coils and/or transmission lines near a body part. The coils may include dielectric and/or ferrite materials which assist in the shaping of the magnetic pulses. Ferrite materials may be used to construct complex dynamic electromagnetic fields for circulators and other circuit elements employed in microwave transmission and receivers (as disclosed by Ansoft Corporation, in Microwave Journal, June, 1996).

Moreover, as disclosed in U.S. patent application Ser. No. 19/488,105 and entitled "Apparatus and Method for Decreasing BioEffects of Magnetic Field Gradients", (incorporated by reference), and discussed above, a plurality of coils may, thus, be used to generate magnetic field gradients. In accordance with further disclosed embodiments, various advantages and applications may be provided by this generation.

For example, although the rise-time of a magnetic field produced by a coil is inversely proportional to the inductance of the coil, and proportional to the voltage applied to the coil, it may be difficult to implement voltages of arbitrary magnitude due to safety requirements or limitations of insulators. Therefore, in accordance with disclosed embodiments, it may be useful and beneficial to segment a coil into separate sections or segments, each one energized by a separate power supply. As a result of such an implementation, the voltage requirement for each power supply may be reduced. Additionally, the inductance for each coil segment may be less than the sum of all the segments, enabling shorter rise- and fall-times as compared to the case in which one power supply was to energize one large coil.

Figure 8:
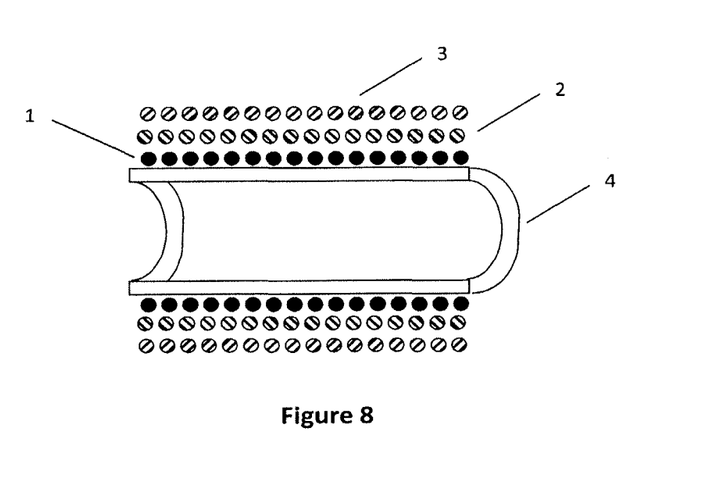
FIG. 8 illustrates a first implementation of a segmented coil contemplated by the disclosed embodiments.

In accordance with disclosed embodiments, the coil segments may be physically overlapping, for example, in the case where each winding or layer on a single mandrel or substrate is attached to a different power supply, as illustrated in FIG. 8.

As shown in FIG. 8, a plurality of coils 1, 2, 3 may overlapping with respect to a mandrel or substrate 4. These coils 1, 2, 3 may be each energized by separate amplifiers.

Figure 9:
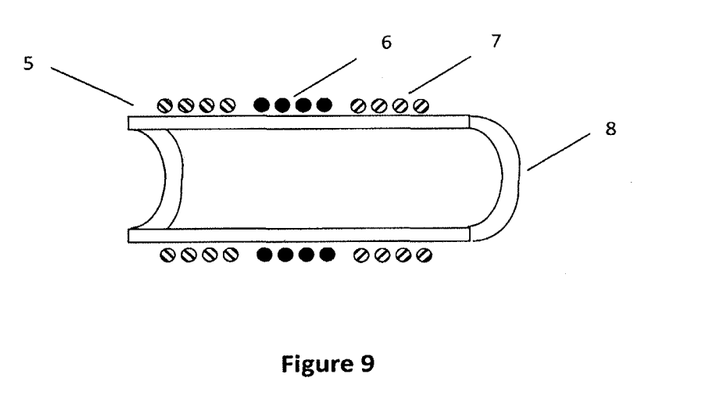
FIG. 9 illustrates a second implementation of a segmented coil contemplated by the disclosed embodiments.

Alternatively, the coil segments may be physically separate, as in the case where the coil segments do not overlap, as illustrated in FIG. 9. As shown in FIG. 9, a plurality of coils 5, 6, 7 are not overlapping with respect to a mandrel or substrate 8, but may each still energized by separate amplifiers.

Figure 10:
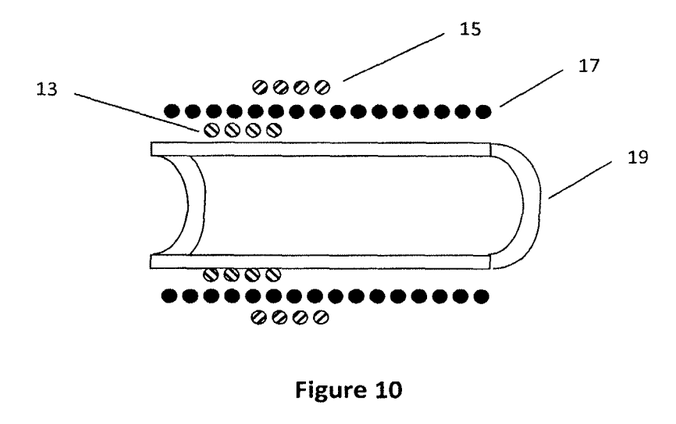
FIG. 10 illustrates a third implementation of a segmented coil contemplated by the disclosed embodiments.

As a further alternative, the coil segments may be partially overlapping as shown in FIG. 10 wherein a plurality of coils 13, 15, 17 are partially overlapping with respect to a mandrel or substrate 19, and which may be each energized by separate amplifiers (e.g., a single power source connected to separate power amplifiers to provide differentiated power levels). It should be understood that the term "power source" encompasses both independent power sources and a single power source coupled to a plurality of power amplifiers to provide power at different power levels, i.e., differentiated power levels, that may be viewed as different power sources.

It should be appreciated that the times at which each coil segment may be activated may be the same or may differ in order to produce different magnetic field gradients.

It should also be understood that switches may be employed to functionally separate amplifiers to drive the separate coils, and that at times these or other switches may be configured so that some or all of the separate coils may be energized by a functionally single amplifier.

Another factor affecting rise time is the skin effect, in which a substantial portion of high-frequency currents traveling through a conductor are forced near the surface of the conductor. Since the cross-sectional area of the conducting channel is reduced by the skin effect, and the resistance of the conductor is inversely proportional to the cross-sectional area of the conducting channel, the resistance of the conductor is effectively increased. Said increased resistance is unwelcome, since it leads to energy loss. In the electrical design community, the energy loss at high frequencies has been addressed through the use of interleaved conductor configurations (also known as wound or "Litz" wire), which effectively increases the cross-sectional area of the interleaved conductor at high frequencies as compared to a solid wire of similar total diameter. The short rise- and fall-times of the contemplated embodiment produce high frequency components, which as discussed above can lead to increased resistance. The rise-time and fall-time of the current is governed by the equation $dI/dt=(V-R*I)/L$, where "I" represents the coil current, "t" is time, "V" is the voltage applied to the coil, "R" is the coil resistance and "L" is the coil inductance. Therefore, reducing the resistance through the use of interleaved conductors in some or all of the coils has a beneficial effect on rise- and fall-time.

Thus, this disclosure enables the delivery of very short multi-phasic magnetic gradient pulses for magnetic resonance imaging. The disclosure also provides a method of decreasing bio-effects in magnetic resonance imaging through the use of reduced pulse lengths and multi-phasic magnetic gradient pulses.

Figure 11:
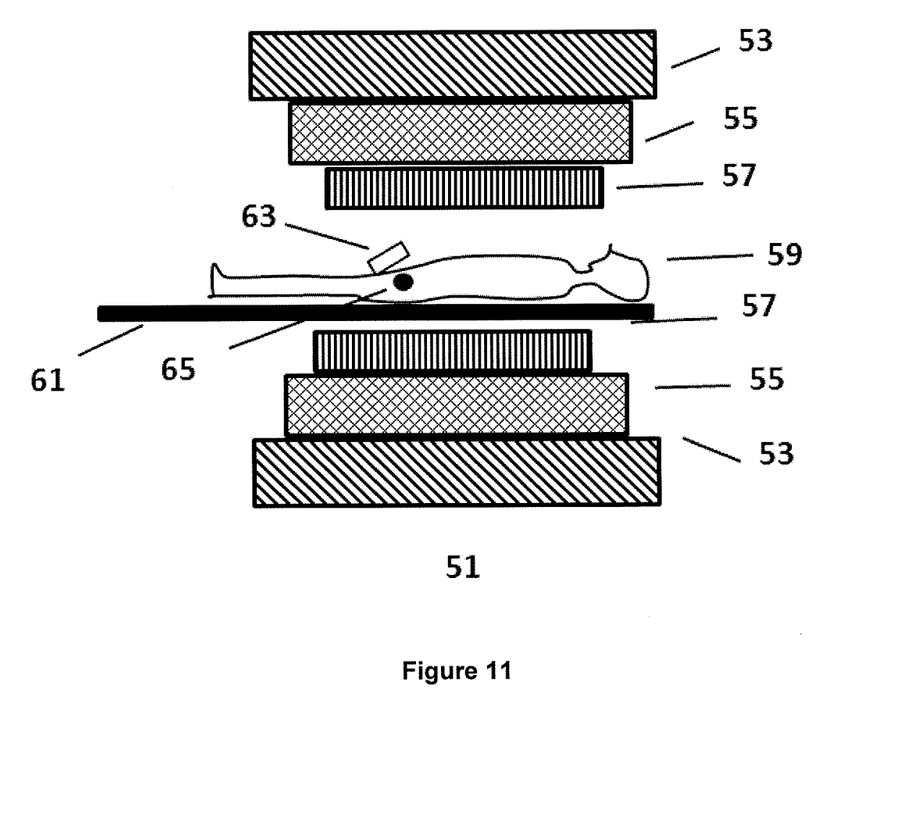
FIG. 11 demonstrates a conventional MRI system with a supplementary gradient coil set according to the disclosed embodiments.

FIG. 11 demonstrates a conventional MRI system with a supplementary gradient coil set, combined as MRI device 51. The conventional MRI is shown with components: permanent magnet 53, native gradient coil 55, radiofrequency coil set 57. The drawing of the device 51 illustrated in FIG. 11 employs symmetry about the patient for the above components, as is typical for MRI systems. It is understood that additional equipment (for example, digitizers and amplifiers), not illustrated in FIG. 11, may be required to operate the illustrated components of a conventional MRI in a pulse sequence to collect images of a body part in a patient 59 resting on a table 61.

A supplementary coil set 63, including gradient and/or radiofrequency antenna elements) may be arrayed near the patient's pelvis (close to the prostate 65) in order to generate fast high pulses for improving spatial resolution and signal-to-noise ratio of the prostate. Additional radiofrequency coils and other ancillary equipment needed to operate the supplementary gradient coil set (for example, amplifiers and digitizers) are understood to potentially be required, and therefore are omitted in FIG. 11.

It should be understood that the magnetic field generated may have either a rise-time or fall-time of less than 100 microseconds or, alternatively, less than 250 microseconds. The magnetic gradient may have a maximum gradient field strength of more than 10 mT/m, 50 mT/m, 100 mT/m, 200 mT/m, 1 T/m. The magnetic gradient may have a maximum slew rate of more than 200 T/m/s, 500 T/m/s, 1000 T/m/s, 1000 T/m/s, or 1 million T/m/s.

The magnitude of the magnetic field may be, for example, more than 50 mT, 100 mT, 200 mT, 300 mT, 400 mT, or 500 mT.

A pulse sequence with multiple fast repetitions may be generated, wherein the repetitions increase the signal-to-noise ratio per pixel. In accordance with at least one embodiment, at least one coil is introduced into a magnetic resonance system to improve visualization of a body part.

Other aspects of the present invention should be apparent to those skilled in the art based on the discussion provided herein.

What is claimed is:

1. A magnetic field generator for imaging, the generator comprising:
    a power source; and
    at least one coil connected to the power source to generate a time-varying magnetic field,
    wherein the time-varying magnetic field has a rise- and fall-time selected so as to be too short to elicit a neurological response in tissue, and
    wherein the time-varying magnetic field has a gradient field strength of more than 1 T/m.

2. The generator of claim 1, wherein the time-varying magnetic field has a field strength of more than 200 mT.

3. The generator of claim 1, wherein each rise- and fall-time of the time-varying magnetic field comprises a pulse and at least one section of a pulse sequence used to collect data about a body part is repeated by the coil more than 100 times per second.

4. The generator of claim 1, wherein each rise- and fall-time of the time-varying magnetic field comprises a pulse and at least one section of a pulse sequence used to collect data about a body part is repeated by the coil more than 1000 times per second.

5. The generator of claim 1, wherein each rise- and fall-time of the time-varying magnetic field comprises a pulse and at least one section of a pulse sequence used to collect data about a body part is repeated by the coil more than 10000 times per second.

6. The generator of claim 1, wherein the at least one coil is introduced into a magnetic resonance system to improve visualization of a body part.

7. The generator of claim 1, wherein the magnitude of the magnetic field is more than 50 mT.

8. The generator of claim 1, wherein the magnitude of the magnetic field is more than 100 mT.

9. The generator of claim 1, wherein the magnitude of the magnetic field is more than 200 mT.

10. A magnetic field generator for imaging, the generator comprising:
    a power source; and
    at least one coil connected to the power source to generate a magnetic field,
    wherein the magnetic field has a rise- and fall-time selected so as to be too short to elicit a neurological response in tissue, and
    wherein the magnitude of the magnetic field is more than 350 mT and a rise-time of less than 250 microseconds.

11. The generator of claim 10, wherein the magnitude of the magnetic field is more than 400 mT.

12. The generator of claim 10, wherein the magnitude of the magnetic field is more than 500 mT.

13. A method of imaging tissue using a magnetic field generator, wherein the generator comprises a power source and at least one coil, the method comprising:
    generating a magnetic field that has a rise- and fall-time selected so as to be too short to elicit a neurological response in tissue,
    wherein the time-varying magnetic field has a field strength of more than 250 mT and a rise-time of less than 100 microseconds.

14. A method of imaging tissue using a magnetic field generator, wherein the generator comprises a power source and at least one coil, the method comprising:
    generating a magnetic field that has a rise- and fall-time selected so as to be too short to elicit a neurological response in tissue
    wherein the magnitude of the magnetic field is more than 400 mT.

15. The method of claim 14, wherein the magnitude of the magnetic field is more than 500 mT.

* * * * *